United States Patent [19]

Pill et al.

[11] Patent Number: 5,679,677
[45] Date of Patent: Oct. 21, 1997

[54] HETEROCYCLIC CARBAMATES, PROCESS FOR THEIR PREPARATION AND MEDICAMENTS

[75] Inventors: Thomas Pill, Siegertsbrunn; Peter Zeiller, München; Wolfram Raake, Baldham; Rainer Klauser, München, all of Germany

[73] Assignee: Luitpold Pharma GmbH, Munich, Germany

[21] Appl. No.: 446,867

[22] PCT Filed: Oct. 4, 1994

[86] PCT No.: PCT/EP94/03280

§ 371 Date: Jun. 5, 1995

§ 102(e) Date: Jun. 5, 1995

[87] PCT Pub. No.: WO95/09842

PCT Pub. Date: Apr. 13, 1995

[30] Foreign Application Priority Data

Oct. 4, 1993 [DE] Germany ............... 43 33 761.9

[51] Int. Cl.⁶ .................. A61K 31/53; C07D 251/00
[52] U.S. Cl. .................. 514/241; 514/309; 514/248; 514/259; 544/220; 544/239; 544/287; 546/141
[58] Field of Search .................. 544/220, 239, 544/287; 514/241, 309, 248, 259; 546/141

[56] References Cited

U.S. PATENT DOCUMENTS 4,769,367  9/1988  Cherry et al. ............... 514/217

FOREIGN PATENT DOCUMENTS

| 1 460 552 | 10/1966 | France . |
| 1 578 785 | 7/1969 | France . |
| 1 807 685 | 8/1970 | Germany . |
| 33 32 996 | 3/1984 | Germany . |
| 59-76069 | 4/1984 | Japan . |
| 6702189 | 8/1968 | Netherlands . |
| 1365806 | 9/1974 | United Kingdom . |

OTHER PUBLICATIONS

Masayuki Ishikawa et al., "Synthetic Studies on Antiatherogenic Agents (I) Syntheses of Carbamate Derivatives of Diazones", *Reports of the Institute for Medical and Dental Engineering*, (1974) 8:9–20.

M. Ishikawa et al., "Synthetic Studies on Antiatherogenic Agents (I) Syntheses of Carbamate Derivatives of Diazones", *Chemical Abstracts*, (1976) 84:462, No. 3 (Abstract).

El–Kafrawy, A.F. et al. "Synthesis and Reactions of 4-(2', 4'-dimethyl)phenyl-5,6, 7,8-tetrachloro-1(2H)-phthalazinone Derivates", *Chemical Abstracts* (1993) 118:879, No. 17 (Abstract).

Hamad M.M. et al., "Some Reactions of 2-(.alpha.-naphthylmethyl)-(4H)-3,1-benzoxazin-4-one" *Chemical Abstracts* (1994) vol. 121, No. 3 (Abstract No. 35525).

Maillard J. et al., "Dérivés de la (3H) Quinazolinnone-4 doues de propriétés anti–inflammatoires; I. Dérivés substitutés en 3 et en 1", *Chimie Therapeutique* (1967) 2:202–212, No. 3.

Ecsery et al., Chemical Abstracts, 73:77272e 1970.

Kosa et al., Chemical Abstracts, 72:79085z 1970.

*Primary Examiner*—Joseph McKane
*Assistant Examiner*—Richard S. Myers, Jr.
*Attorney, Agent, or Firm*—Burns, Doane, Swecker & Mathis, L.L.P.

[57] ABSTRACT

The invention relates to heterocyclic carbamates of the formula (I)

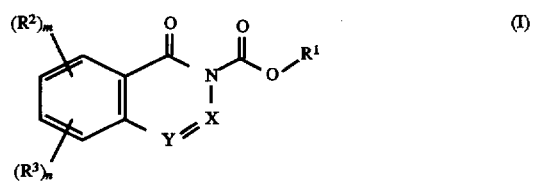

processes for their preparation and medicaments containing them.

15 Claims, No Drawings

HETEROCYCLIC CARBAMATES, PROCESS FOR THEIR PREPARATION AND MEDICAMENTS

The invention relates to compounds of the general formula (I)

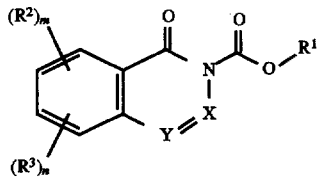

in which a)

X denotes the group $CR^4$ and Y denotes the group $CR^5$ where $R^1$ stands for a $C_1$- to $C_6$- lower alkyl radical, for a substituted $C_1$- to $C_6$- lower alkyl radical, for an aryl-$C_1$- to $C_6$- lower alkyl radical, for an aryl radical or for a heterocyclic radical, $R^2$ and $R^3$ independently of one another stand for radicals of the following meaning:

hydrogen atoms, $C_1$- to $C_6$- lower alkyl radicals, $C_1$- to $C_6$- lower alkoxy radicals, $C_1$- to $C_6$- lower alkylthio radicals, halogen atoms, nitro groups, hydroxyl groups, trifluoromethyl radicals, cyano radicals, sulpho radicals, $C_1$- to $C_6$- lower alkylsulphonyl groups, carboxylic acid groups, $C_1$- to $C_6$- lower alkoxycarbonyl radicals, $C_1$- to $C_6$- lower alkoxycarbonyloxy radicals, acetamido radicals, benzamido radicals or the group $—N(R^6)R^7$, $R^4$ and $R^5$ independently of one another stand for a hydrogen atom, for a $C_1$- to $C_6$- lower alkyl radical, for a substituted $C_1$- to $C_6$- lower alkyl radical, for an aryl-$C_1$- to $C_6$- lower alkyl radical or for an aryl radical, m and n independently of one another are equal to 0, 1, 2, 3, or 4, and $R^6$ and $R^7$ independently of one another stand for a hydrogen atom or a $C_1$- to $C_6$- lower alkyl radical, or in which b)

X and Y denote a nitrogen atom, where $R^1$ stands for a methyl radical, for a $C_3$- to $C_6$- lower alkyl radical, for a substituted $C_1$- to $C_6$- lower alkyl radical, for an aryl-$C_1$- to $C_6$- lower alkyl radical, for an aryl radical or for a heterocyclic radical, $R^2$ and $R^3$ independently of one another stand for radicals of the following meaning:

hydrogen atoms, $C_1$- to $C_6$- lower alkyl radicals, $C_1$- to $C_6$- lower alkoxy radicals, $C_1$- to $C_6$- lower alkylthio radicals, halogen atoms, nitro groups, hydroxyl groups, trifluoromethyl radicals, cyano radicals, sulpho radicals, $C_1$- to $C_6$- lower alkylsulphonyl groups, carboxylic acid groups, $C_1$- to $C_6$- lower alkoxycarbonyl radicals, $C_1$- to $C_6$- lower alkoxycarbonyloxy radicals, acetamido radicals, benzamido radicals or the group $—N(R^6)R^7$, and m and n, $R^6$ and $R^7$ have the meanings mentioned under a), with the proviso that if $R^1$ denotes a methyl radical, an unsubstituted $C_3$- to $C_6$- lower alkyl radical, a phenyl radical or a benzyl radical, at least one radical $R^2$ or $R^3$ is different from a hydrogen atom or a halogen atom, or in which c)

X denotes a nitrogen atom and Y denotes the group $CR^5$, where $R^1$ stands for a substituted $C_1$- to $C_6$- lower alkyl radical, for an aryl-$C_1$- to $C_6$- lower alkyl radical, for an aryl radical or for a heterocyclic radical, $R^2$ and $R^3$ independently of one another have the meanings mentioned under a), $R^5$ stands for a hydrogen atom or for a $C_1$- to $C_6$- lower alkyl radical, and m and n, $R^6$ and $R^7$ have the meanings mentioned under a), or in which d)

X denotes a nitrogen atom and Y denotes the group $CR^5$, where $R^1$ stands for a $C_1$- to $C_6$- lower alkyl radical, for a substituted $C_1$- to $C_6$- lower alkyl radical, for an aryl-$C_1$- to $C_6$- lower alkyl radical, for an aryl radical or for a heterocyclic radical, $R^2$ and $R^3$ independently of one another have the meanings mentioned under a), $R^5$ stands for a substituted $C_1$- to $C_6$- lower alkyl radical, foe an aryl-$C_1$- to $C_6$- lower alkyl radical or for an aryl radical, and m and n, $R^6$ and $R^7$ have the meanings mentioned under a), or in which e)

Y denotes a nitrogen atom and X denotes the group $CR^4$, where $R^1$ stands for a $C_1$- to $C_6$- lower alkyl radical, for a substituted $C_1$- to $C_6$- lower alkyl radical, for an aryl-$C_1$- to $C_6$- lower alkyl radical, for an aryl radical or for a heterocyclic radical, $R^2$ and $R^3$ independently of one another have the meanings mentioned under a), $R^4$ stands for a substituted $C_1$- to $C_6$- lower alkyl radical or for a radical of the general formula (II)

$$—Z—R^8 \quad\quad (II)$$

where Z stands for a carbonyl or carboxyl group, a sulphur atom or an oxygen atom and $R^8$ stands for a $C_1$- to $C_6$- lower alkyl radical, for a substituted $C_1$- to $C_6$- lower alkyl radical, for an aryl-$C_1$- to $C_6$- lower alkyl radical or for an aryl radical, and m and n, $R^6$ and $R^7$ have the meanings mentioned under a), or in which f)

Y denotes a nitrogen atom and X denotes the group $CR^4$, where $R^1$ stands for a substituted $C_1$- to $C_6$- lower alkyl radical, for an aryl radical or for a heterocyclic radical, $R^2$ and $R^3$ independently of one another have the meanings mentioned under a), $R^4$ stands for a hydrogen atom, for a $C_1$- to $C_6$- lower alkyl radical, for a substituted $C_1$- to $C_6$- lower alkyl radical, for an aryl-$C_1$- to $C_6$- lower alkyl radical or for an aryl radical, and m and n, $R^6$ and $R^7$ have the meanings mentioned under a), with the proviso that if $R^2$, $R^3$ and $R^4$ denote hydrogen atoms, $R^1$ is different from an unsubstituted phenyl radical, and their salts with physiologically tolerable acids and bases.

Compounds of the general formula (I) are to be emphasized in which X denotes the group $CR^4$ and Y denotes the group $CR^5$ and $R^1$, $R^2$, $R^3$, $R^4$, $R^5$, m and n have the meanings mentioned under Claim 1a.

Compounds of the general formula (I) are further to be emphasized in which X and Y denote a nitrogen atom and $R^1$, $R^2$, $R^3$ m and n have the meanings mentioned under Claim 1b.

Compounds of the general formula (I) are further to be emphasized in which X denotes a nitrogen atom and Y denotes the group $CR^5$ and $R^1$, $R^2$, $R^3$, $R^5$, m and n have the meanings mentioned under Claim 1c.

Compounds of the general formula (I) are further to be emphasized in which X denotes a nitrogen atom and Y denotes the group $CR^5$ and $R^1$, $R^2$, $R^3$, $R^5$, m and n have the meanings mentioned under Claim 1d.

Compounds of the general formula (I) are further to be emphasized in which Y denotes a nitrogen atom and X denotes the group $CR^4$ and $R^1$, $R^2$, $R^3$, $R^4$, $R^8$, m and n have the meanings mentioned under Claim 1e.

For the various substituents or radicals mentioned in connection with the present application description the following explanations apply:

Examples of $C_1$- to $C_6$- lower alkyl radicals are unbranched and branched hydrocarbon radicals having one to six carbon atoms such as methyl radicals, ethyl radicals, n-propyl radicals, isopropyl radicals, n-butyl radicals, isobutyl radicals, 1-methylpropyl radicals, tert-butyl radicals, n-pentyl radicals, 1-methylbutyl radicals, 2-methylbutyl radicals, 3-methylbutyl radicals, 1,1-dimethylpropyl radicals, 2,2-dimethylpropyl radicals, 1,2-dimethylpropyl radicals, 1-ethylpropyl radicals, n-hexyl radicals, 1-methylpentyl radicals, 2-methylpentyl radicals, 3-methylpentyl radicals, 4-methylpentyl radicals, 1,1-dimethylbutyl radicals, 2,2-dimethylbutyl radicals, 3,3-dimethylbutyl radicals, 1,2-dimethylbutyl radicals, 2,3-dimethylbutyl radicals, 1,3-dimethylbutyl radicals, 1-ethylbutyl radicals, 2-ethylbutyl radicals, 1,1,2-trimethylpropyl radicals, 1,2,2-trimethylpropyl radicals, 1-ethyl-2-methylpropyl radicals or 1-ethyl-1-methylpropyl radicals. Methyl radicals, ethyl radicals, n-propyl radicals, isopropyl radicals, n-butyl radicals or isobutyl radicals are preferred here. Ethyl radicals, isopropyl radicals and isobutyl radicals are particularly preferred.

If in the present application the expression "lower alkyl" appears on its own or in combination with other functional groups (e.g. lower alkoxy, lower alkoxy-carbonyl, or lower alkylthio groups), this expression has the definitions indicated above.

Examples of substituted $C_1$- to $C_6$- lower alkyl radicals are the abovementioned lower alkyl radicals having one to six carbon atoms, which are substituted once or twice by identical or different radicals from those mentioned in the following: hydroxyl radicals, $C_3$- to $C_6$- lower alkoxy radicals, $C_1$- to $C_6$- lower alkoxy-carbonyl radicals, $C_1$- to $C_6$- lower alkylthio radicals, halogen atoms, nitro groups, cyano radicals, sulpho radicals, $C_1$- to $C_6$- lower alkylsulphonyl radicals, carboxylic acid groups, di-$C_1$- to $C_6$- lower alkylamino radicals, acetamido radicals and benzamido radicals. 2-Hydroxyethyl radicals, 2-methoxyethyl radicals, ethoxy-carbonylmethyl radicals, methoxycarbonylmethyl radicals, 2-ethoxycarbonylethyl radicals, acetic acid and 3-propionic acid radicals, 2-dimethylaminoethyl radicals, 3-dimethylaminopropyl radicals, 2-acetamidoethyl radicals and 2-benzamidoethyl radicals are preferred here. The 2-hydroxyethyl radical, the ethoxycarbonylmethyl radical, the methoxycarbonylmethyl radical, the 2-dimethylaminoethyl radical and the 2-acetamidoethyl radical are particularly preferred.

Examples of aryl radicals are the phenyl radical or the phenyl radical substituted once, twice or three times by identical or different radicals from those mentioned below: $C_1$- to $C_6$- lower alkyl radicals, $C_1$- to $C_6$- lower alkoxy radicals, $C_1$- to $C_6$- lower alkoxycarbonyl radicals, $C_1$- to $C_6$- lower alkylthio radicals, hydroxyl radicals, halogen atoms, nitro groups, trifluoromethyl radicals, cyano radicals, sulpho radicals, alkylsulphonyl radicals, carboxylic acid groups, dialkylamino radicals, acetamido radicals, benzamido radicals, phenyl radicals. Phenyl radicals, 2-fluorophenyl radicals, 3-fluorophenyl radicals, 4-fluorophenyl radicals, 2-chlorophenyl radicals, 3-chlorophenyl radicals, 4-chlorophenyl radicals, 2-bromophenyl radicals, 3-bromophenyl radicals, 4-bromophenyl radicals, 2-iodophenyl radicals, 3-iodophenyl radicals, 4-iodophenyl radicals, 2-methoxyphenyl radicals, 3-methoxyphenyl radicals, 4-methoxyphenyl radicals, 2-methoxycarbonylphenyl radicals, 3-methoxycarbonylphenyl radicals, 4-methoxycarbonylphenyl radicals, 2-methylphenyl radicals, 3-methylphenyl radicals, 4-methylphenyl radicals, 2-trifluoromethylphenyl radicals, 3-trifluoromethylphenyl radicals, 4-trifluoromethylphenyl radicals, 2,4-dichlorophenyl radicals, 3,4-dichlorophenyl radicals, 2,3-dichlorophenyl radicals, 2,5-dichlorophenyl radicals, 2,4-dibromophenyl radicals, 3,4-dibromophenyl radicals, 5 2,3-dibromophenyl radicals, 2,5-dibromophenyl radicals, 2,4-dimethoxyphenyl radicals, 3,4-dimethoxyphenyl radicals, 2,3-dimethoxyphenyl radicals, 2,5-dimethoxyphenyl radicals, 2,4-dimethylphenyl radicals, 3,4-dimethylphenyl radicals, 2,3-dimethylphenyl radicals, 2,5-dimethylphenyl radicals, 2-ethylthiophenyl radicals, 3-ethylthiophenyl radicals, 4-ethylthiophenyl radicals, 2-dimethylaminophenyl radicals, 3-dimethylaminophenyl radicals, 4-dimethylaminophenyl radicals, 2-acetamidophenyl radicals, 3-acetamidophenyl radicals and 4-acetamidophenyl radicals are preferred here. The phenyl radical, the 4-chlorophenyl radical, the 2-methoxyphenyl radical, the 4-methoxyphenyl radical, the 2-methoxycarbonylphenyl radical, the 4-methoxycarbonylphenyl radical, the 2-trifluoromethylphenyl radical, the 2,4-dichlorophenyl radical, the 2,4-dimethoxyphenyl radical and the 4-acetamidophenyl radical are particularly preferred. The phenyl radical, the 2-methoxyphenyl radical, the 4-methoxyphenyl radical, the 2-methoxycarbonylphenyl radical and the 4-methoxycarbonylphenyl radical are very particularly preferred.

Aryl-$C_1$- to $C_6$- lower alkyl radicals are the $C_1$- to $C_6$- lower alkyl radicals defined above, linked to an aryl radical which is as defined above. Examples of aryl-lower alkyl radicals are benzyl radicals, phenethyl radicals, 4-fluorobenzyl radicals, 2-(4-fluorophenyl)-ethyl radicals, 4-chlorobenzyl radicals, 2-(4-chlorophenyl)ethyl radicals, 4-bromobenzyl radicals, 2-(4-bromophenyl)ethyl radicals, 4-iodobenzyl radicals, 2-(4-iodophenyl)ethyl radicals, 2-hydroxybenzyl radicals, 2-(2-hydroxyphenyl)ethyl radicals, 3-hydroxybenzyl radicals, 2-(3-hydroxyphenyl)ethyl radicals, 4-hydroxybenzyl radicals, 2-(4-hydroxyphenyl)ethyl radicals, 2-methoxybenzyl radicals, 2-(2-methoxyphenyl)ethyl radicals, 4-methoxybenzyl radicals, 2-(4-methoxyphenyl)ethyl radicals, 4-ethoxybenzyl radicals, 2-(4-ethoxyphenyl)ethyl radicals, 4-tert-butoxybenzyl radicals, 2-(4-tert-butoxyphenyl)ethyl radicals, 2,5-dimethoxybenzyl radicals, 2,4-dimethoxybenzyl radicals, 4-methylbenzyl radicals, 2-(4-methylphenyl)ethyl radicals, 4-nitrobenzyl radicals, 2-(4-nitrophenyl)ethyl radicals, 2-dimethylaminobenzyl radicals, 4-dimethylaminobenzyl radicals, 2-(4-dimethylaminophenyl)ethyl radicals, 2-trifluoromethylbenzyl radicals, 3-trifluoromethylbenzyl radicals, 4-trifluoromethylbenzyl radicals, 2-methoxycarbonylbenzyl radicals, 4-methoxycarbonylphenyl radicals, 4-ethylmercaptobenzyl radicals or 2-methoxy-5-methylbenzyl radicals.

Preferred aryl-$C_1$- to $C_6$- lower alkyl radicals are benzyl radicals, phenethyl radicals, 4-fluorobenzyl radicals, 4-chlorobenzyl radicals, 4-bromobenzyl radicals, 4-iodobenzyl radicals, 2-methoxybenzyl radicals, 4-methoxybenzyl radicals, 2-ethoxybenzyl radicals, 4-ethoxybenzyl radicals, 2,5-dimethoxybenzyl radicals, 2,4-dimethoxybenzyl radicals, 2-methylbenzyl radicals, 4-methylbenzyl radicals, 2-methoxycarbonylbenzyl radicals, 4-methoxycarbonylbenzyl radicals, 2-dimethylaminobenzyl radicals, 4-dimethylaminobenzyl radicals, 2-trifluoromethylbenzyl radicals, 3-trifluoromethylbenzyl radicals, 4-trifluoromethylbenzyl radicals, 2-acetamidobenzyl radicals and 4-acetamidobenzyl radicals.

The benzyl radical, the 4-chlorobenzyl radical, the 2-methoxybenzyl radical, the 2-ethoxybenzyl radical, the 2,4-dimethoxybenzyl radical, the 2-methoxycarbonylbenzyl radical, the 2-dimethylaminobenzyl radical, the 2-trifluoromethylbenzyl radical, the 2-acetamidophenyl radical, and the 4-acetamidobenzyl radical are particularly preferred.

The benzyl radical, the 2-methoxybenzyl radical and the 2-trifluoromethylbenzyl radical are very particularly preferred.

Examples of halogen atoms are fluorine, chlorine, bromine or iodine atoms.

Examples of a heterocyclic radical are radicals of saturated 5- or 6-membered monocyclic heterocyclic rings which contain one, two or three identical or different heteroatoms such as nitrogen atoms, oxygen atoms or sulphur atoms.

Tetrahydrofuran-3-yl radicals, tetrahydropyran-4-yl radicals, N-methylpiperidin-3-yl radicals and N-methylpiperidin-4-yl radicals are preferred. The tetrahydrofuran-3-yl radical and the N-methylpiperidin-3-yl radical are particularly preferred.

Examples of radicals $R^4$ in which $R^4$ has the meaning of the general formula (II) are methylcarbonyl radicals, propylcarbonyl radicals, methoxycarbonyl radicals, ethoxycarbonyl radicals, methylthio radicals ethylthio radicals, benzylthio radicals, methoxycarbonylmethylthio radicals, methoxy radicals, ethoxy radicals, benzyloxy radicals, methoxycarbonylmethoxy radicals. Ethylthio radicals, benzylthio radicals, methoxycarbonyl radicals, ethoxycarbonyl radicals and methoxycarbonylmethylthio radicals are preferred.

If the compounds according to the invention are present in salt form, these are in this case salts with physiologically tolerable inorganic or organic acids and bases. Examples of salts with physiologically tolerable bases are ammonium, sodium, potassium, lithium, magnesium and calcium salts, and also salts which ethanolamine, triethanolamine, morpholine or piperidine. Examples of salts with physiologically tolerable acids are citrate-, tartrate-, acetate-, fumarate-, gluconate-, glutamate-, lactate-, malate-, maleate-, mesylate-, succinate-, carbonate-, hydrogencarbonate-, hydrogen-, sulphate-, phosphate-, hydrogenphosphate-, dihydrogen-, phosphate-, chloride-, and bromide-containing salts.

The synthesis of compounds of the general formula (I) is carried out in analogy to processes known from the literature. The invention therefore also relates to a process for the preparation of compounds of the general formula (I), which is characterized in that a compound of the general formula (III)

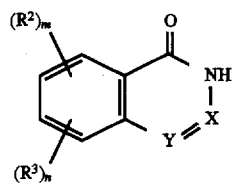

in which X, Y, $R^2$, $R^3$, m and n have the abovementioned meanings, is reacted with haloformic acid esters of the general formula (IV)

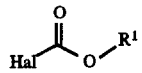

in which $R^1$ has the abovementioned meaning and Hal has the meaning fluorine or chlorine atoms, according to the following reaction scheme:

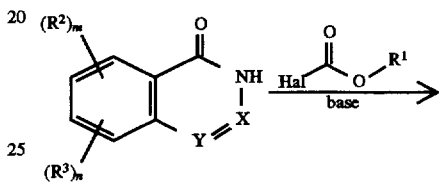

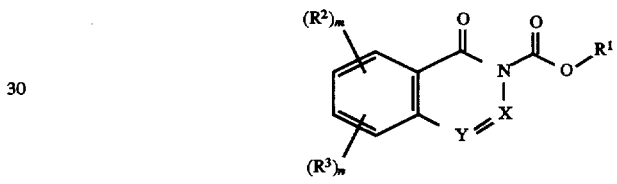

Bases used can be both organic and inorganic bases, for example tertiary amines, pyridine, sodium acetate, sodium and potassium hydroxide, sodium and potassium carbonate, sodium and potassium hydrogen-carbonate, sodium and calcium hydride and elemental sodium or potassium. Triethylamine, sodium carbonate and sodium hydride are particularly preferred here. (Compare the references: e.g. U. Petersen in Houben-Weyl, Methoden der Organischen Chemie [Methods of Organic Chemistry], Volume E4, Kohlensäurederivate [Carbonic acid derivatives], p. 142 ff, Georg Thieme Verlag, Stuttgart 1983 and references cited there).

Depending on the base used, methylene chloride, chloroform, toluene, ethyl acetate, acetone, tetrahydrofuran, dimethylformamide, pyridine or acetonitrile can be used as solvents. Methylene chloride, toluene, acetone and tetrahydrofuran are particularly preferred here.

Depending on the compound, the reactions are carried out with ice cooling, at room temperature or at the boiling point of the respective solvent.

Alternatively, a compound of the general formula (III) is reacted with an appropriate carbonic acid diester of the general formula (V)

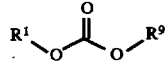

in which $R^1$ has the abovementioned meaning and $R^9$ is either identical with $R^1$ or forms a suitable leaving group $R^9O^-$, such as e.g. electronegatively substituted phenoxy groups, (e.g. 4-nitro-, 2-nitro-, 2,4-dinitro-, 2,3,5-trichloro-, or 4-acetylphenoxy) or suitable hydroxylamines (e.g. 1-hydroxypiperidine, N-hydroxysuccinimide or N-hydroxyphthalimide), according to the following reaction scheme:

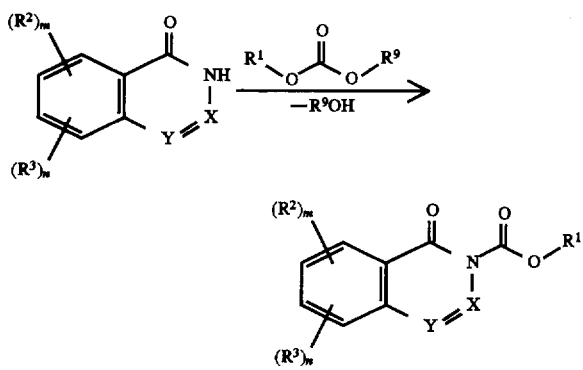

The reaction is carried out at about 100°–150° C. by fusion of the two components or in a high-boiling solvent such as dimethylformamide or dimethyl sulphoxide.

In the case where in the compounds of the general formula (I) according to the invention the radicals $R^1$, $R^2$, $R^3$, $R^4$, $R^5$ and $R^8$ contain reactive groups such as hydroxyl groups, mercapto groups, amino groups or carboxylic acid radicals, these groups must be protected by protective groups in a suitable manner before the reaction. Methods for the protection of these reactive groups are described in Theodora W. Greene, Protective Groups in Organic Synthesis, John Wiley & Sons, New York 1981.

The corresponding starting compounds having the general formula (III)

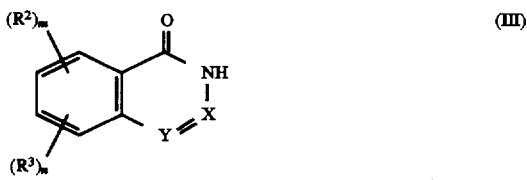

in which X, Y, $R^2$, $R^3$, m and n have the abovementioned meanings, are prepared following various methods known from the literature:

isoquinolin-1(2 H)-one (X=$CR^4$, Y=$CR^5$): Beilstein 21, 100; Beilstein 21 (3), 2245; G. S. Poindexter, J. Org. Chem. 47 (1982.) 3787 and references cited there; A. Couture, H. Cornet, P. Grandclaudon, J. Organomet. Chem. 440 (1992) 7 and references cited there.

1,2,3-Benzotriazin-4(3 H)-one (X=N, Y=N): Beilstein 26, 163; A. Weddige, H. Finger, J. Prakt. Chem. 35 (1887) 262; H. Finger, J. Prakt. Chem. 37 (1888) 431; E. Zacharias, J. Prakt. Chem. 43 (1891) 446; D. Binder, Ch. R. Noe, F. Hillebrand, Arch. Pharm. 312 (1979) 845. 1(2 H)-Phthalazinone (X=N, Y=$CR^5$): Beilstein 24, 142; S. Gabriel, A. Neumann, Chem. Ber. 26 (1893) 523; v. Rothenburg, J. Prakt. Chem. 51 (1895) 147; C. Liebermann, A. Bistrzycki, Chem. Ber. 26 (1893) 535. Quinazolin-4(3 H)-one (X=$CR^4$, Y=N): Beilstein 24, 143; R. Pech, R. Böhm, Pharmazie 44 (1989) 790; A. Ebenreth, R. Pech, R. Böhm, Pharmazie 47 (1992) 488; K. Hemender Reddy, A. Panduranga Reddy, V. Veeranagaiah, Indian J. Chem. 31B (1992) 163; C. G. Dave, P. R. Shah, A. B. Shah, Indian J. Chem. 31B (1992) 492.

Compounds of the general formula (IV) and also of the general formula (V) are obtained by reaction of the corresponding alcohols with phosgene, with trichloromethyl chloroformate or with bis(trichloromethyl) carbonate. Following methods known from the literature (compare the reference: e.g. G. Heywang in Houben-Weyl, Methoden der Organischen Chemie [Methods of Organic Chemistry], Volume E4, Kohlensäurederivate [Carbonic acid 5 derivatives], p. 9 ff, Georg Thieme Verlag, Stuttgart 1983 and references cited there; U. Petersen, ditto, p. 64 ff), the phosgene in this case can be allowed to act directly on lower alcohols, or both components are reacted with a base such as triethylamine or pyridine in an inert solvent such as methylene chloride or diethyl ether and, depending on the stoichiometry, compounds of the general formula (IV) or (V) are obtained.

The compounds of the general formula (I) are useful pharmaceutical active compounds. As the applicant has surprisingly found, the compounds according to the invention are distinguished by a good antithrombotic activity; they are free of undesired properties and thus very highly tolerable. These compounds are further potent inhibitors of enzymes breaking down connective tissue, in particular granulocyte elastase.

Compounds having a similar structure to the compounds according to the invention are known from the prior art (NL Patent 6702189; DE-OS 1807685; Bull. Korean Chem. Soc. 11, 7 (1990); Reports Inst. Med. Dent. Eng. 8, 9 (1974); FR Patent 1460552). However, other actions of these known compounds are described than the compounds according to the invention have.

Recently, the following relevant references have also been disclosed: CH Patent 540 266; FR Patent 1578785; JP Kokai 73 62,782; Chim. Ther. 2, 202–212 (1967); GB Patent 1 365 806; JP Kokai 73 80,581; DE AS 2 451 417 and JP A2 59-76069.

The actions of the compounds according to the invention make possible their use for the prevention and treatment of thromboembolic disorders or conditions and further for the prevention and treatment of diseases which are associated with excessive breakdown of connective tissue, in particular of the articular cartilage. Examples of thromboembolic disorders in which the use of the substances according to the invention is advantageous are deep and superficial venous thromboses and arterial thromboses such as cardiac infarct or ischaemic brain disorders.

Diseases which can be mentioned which are associated with excessive breakdown of connective tissue and which can be treated with the compounds according to the invention are especially arthritides and arthroses and also muscular dystrophy and pulmonary emphysema. A further syndrome which can be successfully treated with the elastase inhibitors according to the invention is disseminated intravasal coagulation (DIC) which can occur in septic or traumatic shock or in burns.

In investigations on the antithrombotic action in the tail-bleeding time model on the rat in a modified test according to Diness (V. Diness et al., Thrombos. Haemostas. 55 (1986) 410–414) on groups of 10 rats, compounds according to the invention proved to be highly active on oral administration. The compound from Example 14 at a dose of 200 mg/kg thus prolonged the bleeding time by 103%.

The inhibition of granulocyte elastase was determined in an enzyme inhibition test using elastase from human granulocytes. In this test the specific substrate L-pyroglutaminyl-L-prolyl-L-valine-p-nitro-anilide was used (J. A. Kramps et al., Scand. J. Lab. Invest. 43 (1983) 427–432). The $IC_{50}$ values (concentrations for 50% inhibition) are shown in Table 1 for exemplary compounds according to the invention.

TABLE 1

Inhibition of granulocytic elastase

| Compound from example | IC$_{50}$ (μM) |
| --- | --- |
| 1 | 0.20 |
| 2 | 0.30 |
| 4 | 8.30 |
| 6 | 0.75 |
| 13 | 4.00 |
| 14 | 6.00 |
| 15 | 5.40 |

The invention therefore also relates to medicaments for the treatment of humans and animals, consisting of or containing one or more compounds of the general formula (I), if appropriate together with customary excipients and auxiliaries.

The compounds according to the invention can be administered in a multiplicity of pharmaceutical preparation forms and formulations, such as, for example, tablets, coated tablets, capsules, pills, granules, liquid preparations to be administered orally, suppositories, solutions, suspensions and emulsions, pastes, ointments, gels, crees, lotions, patches, injection solutions, powders, sprays or aerosols, it being possible to use generally customary excipients and auxiliaries which are compatible with the compounds according to the invention.

Besides the compounds of the general formula (1), the medicaments according to the invention preferably contain non-toxic, inert pharmaceutically suitable excipients and auxiliaries. Non-toxic, inert pharmaceutically suitable excipients and auxiliaries are to be understood as meaning solid, semisolid or liquid diluents, fillers and formulation auxiliaries of any type.

Tablets, coated tablets, capsules, pills and granules may contain the active compound or compounds together with the customary excipients. These include a) fillers and extenders, for example starches, lactose, cane sugar, glucose, mannitol, and silicic acid, b) binders, for example carboxymethylcellulose, alginates, gelatin, polyvinylpyrrolidone, c) humectants, for example glycerol, d) disintegrants, for example agaragar, calcium carbonate and sodium hydrogencarbonate, e) solution retardants, for example paraffin, f) absorption accelerators, g) wetting agents, for example cetyl alcohol, glycerol monostearate, h) adsorbents, for example kaolin and bentonite and i) lubricants, for example talc, calcium and magnesium stearate and solid polyethylene glycols or mixtures of the substances mentioned under a) to i).

The tablets, coated tablets, capsules, pills and granules can be provided with customary covering coatings which optionally contain opacifying agents and are also thus composed such that they release the active compound or compounds only or preferably in a certain part of the intestinal tract, if appropriate with a delay, it being possible to use, for example, polymeric substances and waxes as embedding materials. The active compound or compounds can optionally also be present in microencapsulated form with one or more of the excipients indicated above.

Besides the active compound or compounds, suppositories can contain the customary water-soluble or water-insoluble excipients, for example polyethylene glycols, fats, for example cocoa fat, and higher esters (for example $C_{14}$-alcohol with $C_{16}$-fatty acid or mixtures of these substances).

In addition to the active compound or compounds, as an oily base creams primarily contain fatty alcohols, for example lauryl, cetyl, or stearyl alcohol, fatty acids, for example palmitic or stearic acid, liquid to solid waxes, for example isopropyl myristate, wool wax or beeswax and/or hydrocarbons, for example petroleum jelly (petroleum) or liquid paraffin. Emulsifiers used are preferably those having mainly hydrophilic properties, for example non-ionic emulsifiers such as fatty acid esters of polyalcohols, ethylene oxide adducts of polyalcohols such as polyglycerol fatty acid esters or polyoxyethylene sorbitan fatty acid esters (Tweens) or ionic emulsifiers such as alkali metal salts of fatty alcohol sulphates, for example sodium lauryl sulphate, sodium cetyl sulphate or sodium stearyl sulphate. Agents can be added to the water phase which prevent the drying out of the cream, for example polyalcohols such as glycerol, sorbitol, propylene glycol and/or polyethylene glycols.

Besides the active compound or compounds, possible excipients for ointments are primarily hydrocarbons, for example petroleum jelly or liquid paraffin, which for improving the water-binding power preferably contain suitable fatty alcohols or esters thereof, for example cetyl alcohol or wool wax. Emulsifiers are appropriate lipophilic substances such as sorbitan fatty acid esters. Humectants such as, for example, glycerol or propylene glycol can be added to the water phase.

Besides the active compound or compounds sprays and powders can contain the customary excipients, for example lactose, talc, silicic acid, alumina, calcium silicate and polyamide powder or mixtures of these substances. Sprays can additionally contain the customary propellants.

Besides the-active compound or compounds, solutions and emulsions can contain the customary excipients such as solvents, solubilizers and emulsifiers, for example water, ethanol, isopropanol, ethyl carbonate, benzyl alcohol, benzyl benzoate, propylene glycol, 1,3-butylene glycol, oils, in particular cottonseed oil, groundnut oil, maize oil, castor oil, cashew nut oil and sesame oil, glycerol, glycerol formal, polyethylene glycols and fatty acid esters of sorbitan or mixtures of these substances.

Besides the active compound or compounds, suspensions can contain the customary excipients such as liquid diluents, for example ethanol, propylene glycol, suspending agents, for example ethoxylated isostearyl alcohol's, polyoxyethylene sorbitol and sorbitan esters, microcrystalline cellulose, aluminium metahydroxide, bentonite, agar-agar or tragacanth or mixtures of these substances.

The said formulation forms can also contain colourants, preservatives and also smell- and taste-improving additives, for example peppermint oil and eucalyptus oil and sweeteners, for example saccharin.

The compounds according to the invention are preferably contained in the abovementioned pharmaceutical preparations in a concentration of about 0.1 to 99.5, particularly preferably of about 0.5 to 95, % by weight of the total mixture.

Apart from the active compounds according to the invention, the abovementioned pharmaceutical preparations can also contain further pharmaceutical active compounds.

The abovementioned pharmaceutical preparations are prepared in a customary manner by known methods, for example by mixing the active compounds with the excipients.

The present active compounds or pharmaceutical preparations, which contain one or more active compounds, can be employed in human and veterinary medicine for the prevention, amelioration and/or cure of thromboembolic diseases or conditions, or of diseases in which an excessive breakdown of connective tissue is of importance.

In general, it has proven advantageous in human medicine to use the active compound or compounds according to the invention in total doses of about 1 to about 2000 mg, preferably 5 to 1000 mg, daily, in particular one to four dose units per day being administered to achieve the desired results.

However, it may be necessary to depart from the dosages mentioned, mainly depending on the species and the body weight of the subject to be treated, the nature and the severity of the disorder, the manner of preparation and administration of the medicament and the period or interval within which administration takes place. Thus, in some cases it may be adequate to manage with less than the abovementioned amount of active compound, while in other cases the abovementioned amount of active compound must be exceeded.

The following examples illustrate the invention in greater detail without restricting its scope.

EXAMPLES

Example 1

Phenyl 1(2 H)-phthalazinone-N-carboxylate 4.38 g (30 mmol) of 1(2 H)-phthalazinone and 4.16 ml (30 mmol) of triethylamine are dissolved in 150 ml of dichloromethane and a solution of 3.33 ml (35 mmol) of ethyl chloroformate is added dropwise at 0° C. in 50 ml of dichloromethane. After stirring at room temperature for 12 hours, the solution obtained is washed three times with 50 ml of water in each case and dried over sodium sulphate, and the solvent is removed. The residue crystallizes completely after some time. Alternatively, it is stirred with diisopropyl ether until complete crystallization. Subsequent recrystallization from ethanol yields the title compound in 76% yield. Colourless crystals; m.p.: 74° C.

$^1$H-NMR (CDCl$_3$): δ(ppm)=7.28–8.54 (m; Ar—H).

IR (Nujol; cm$^{-1}$): 3045, 3025, 1784, 1775(sh), 1693, 1670 (sh), 1600, 1486, 1321, 1297, 1268, 1241, 1208, 1192, 1168, 1154, 761, 748, 719, 688, 682.

Examples 2–14:

In analogy to the above procedure, the following title compounds are obtained by reaction of the respective starting compounds ((Isoquinolin-1(2H)-one, 1,2,3-benzotriazin-4(3 H)-one, 1(2 H)-phthalazinone/-derivatives or quinazolin-4(3 H)-one/derivatives) with the appropriate chloroformic acid esters. Crystallization or purification is carried out by stirring in a suitable solvent such as .petroleum ether, diisopropyl ether or diethyl ether, by recrystallization in solvents such as cyclohexane, toluene, xylene, diisopropyl ether, tert-butyl methyl ether, ethanol or isopropanol or by column chromatography:

| Ex. No. | Starting Compound | Haloformic acid ester | Title compound | M.p. (°C.) |
|---|---|---|---|---|
| 2 | 2-vinylbenzamide | chloroformic acid ethyl ester | N-(ethoxycarbonyl)-2-vinylbenzamide | oil |
| 3 | 2-(phenyldiazenyl)benzohydrazide | chloroformic acid isobutyl ester | isobutyl carbazate derivative | 76 |
| 4 | 2-(phenyldiazenyl)benzohydrazide | 4-(methoxycarbonyl)phenyl chloroformate | corresponding carbazate | 143 |
| 5 | 2-vinylbenzohydrazide | 2-(methoxycarbonyl)phenyl chloroformate | corresponding carbazate | 112 |
| 6 | 2-(1-methylvinyl)benzohydrazide | phenyl chloroformate | corresponding carbazate | 192 |

-continued

| Ex. No. | Starting Compound | Haloformic acid ester | Title compound | M.p. (°C.) |
|---|---|---|---|---|
| 7 | | | | 137 |
| 8 | | | | 118 |
| 9 | | | | 72 |
| 10 | | | | 58 |
| 11 | | | | oil |

-continued

| Ex. No. | Starting Compound | Haloformic acid ester | Title compound | M.p. (°C.) |
|---|---|---|---|---|
| 12 | benzamide with S-CH2-C(O)-O-CH3 imino group | phenyl chloroformate | phenoxycarbonyl derivative with S-CH2-C(O)-O-CH3 | 92 |
| 13 | benzamide with S-CH2-phenyl imino group | phenyl chloroformate | phenoxycarbonyl derivative with S-benzyl | 72 |
| 14 | benzamide with S-CH2-phenyl imino group | ethyl chloroformate | ethoxycarbonyl derivative with S-benzyl | 35 |

Example 15:
Ethyl 5-ethoxycarbonyloxyisoquinolin-1(2 H)-one-N-carboxylate 4.83 g (30 mmol) of 1,5-isoquinolinediol and 8.32 ml (60 mmol) of triethylamine are dissolved in 150 ml of dichloromethane and a solution of 6.67 ml (70 mmol) of ethyl chloroformate is added dropwise at 0° C. in 50 ml of dichloromethane. After stirring at room temperature for 12 hours the solution obtained is washed twice with 50 ml of 2 N sodium hydroxide solution in each case and three times with 50 ml of water in each case and dried over sodium sulphate, and the solvent is removed. The residue crystallizes after some time and is stirred with petroleum ether until complete crystallization. The title compound is obtained in 82% yield.
Colourless crystals; m.p.: 71° C.
$^1$H-NMR (CDCl$_3$): δ(ppm)=1.40 (t, $^3$J=7 Hz; 3 H, —CH$_2$—CH$_3$), 1.46 (t, $^3$J=7 Hz; —CH$_2$—CH$_3$), 4.35 (q, $^3$J=7 Hz; 2H, —CH$_2$—CH$_3$), 4.53 (q, $^3$J=7 Hz; 2H, —CH$_2$—CH$_3$), 6.56

IR (Nujol; cm$^{-1}$): 3115, 3058, 2778, 1774, 1736, 1684, 1632, 1602, 1461, 1404, 1310, 1282, 1258, 1249, 1224, 1199, 1169, 1132, 1096, 1083, 1060, 1022, 997, 961, 882, 861, 782, 768, 683.

Examples 17–18

As described in Example 16, the following title compounds are obtained by reaction of the respective starting compounds (1,2,3-benzotriazin-4(3 H)-one, 1(2 H)-phthalazinone) with the appropriate alcohols and with trichloromethyl chloroformate ("diphosgene"). Crystallization or purification is carried out by stirring in a suitable solvent such as petroleum ether, diisopropyl ether or diethyl ether, by recrystallization in solvents such as cyclohexane, toluene, xylene, diisopropyl ether, tert-butyl methyl ether, ethanol or isopropanol or by column chromatography:

| Ex. No. | Starting Compound | Haloformic acid ester | Title compound | M.p. (°C.) |
|---|---|---|---|---|
| 17 | | | | 112 |
| 18 | | | | 118 |

(d, $^3$J=8 Hz; 1 H, R$^5$=H), 7.43–7.70 (m; 4 H, C—H$_{aromat}$), 8.31 (d, $^3$J=8 Hz; 1 H, R$^4$=H)
IR (Nujol; cm$^{-1}$): 3135, 3115, 1754, 1734, 1694, 1640, 1609, 1562, 1310, 1279, 1259, 1233, 1177, 1148, 1136, 1114, 1086, 1057, 1000, 956, 924, 912, 887, 860, 850 820, 769, 756, 739, 720, 700, 689, 637.

Example 16:
N'-Methylpiperidin-3-yl isoquinolin-1(2 H)-one-N-carboxylate

A solution of 4.04 ml (35 mmol) of 3-hydroxy-N-methylpiperidine and 4.85 ml (35 mmol) of triethylamine in 50 ml of dichloromethane is added dropwise at 0° C. to a solution of 2.11 ml (17.5 mmol) of trichloromethyl chloroformate ("diphosgene") in 150 ml of dichloromethane and the mixture is then stirred at room temperature for 3 hours. 4.35 g (30 mmol) of solid isoquinolin-1(2 H)-one ("isocarbostyril") are added to the resulting colourless suspension with ice cooling, a solution of 4.15 ml (30 mmol) of triethylamine in 50 ml of dichloromethane is added dropwise and the mixture is stirred overnight at room temperature. The solution, which is now clear, is washed once with 50 ml of half-saturated sodium hydrogen carbonate solution and three times with 50 ml of water in each case, dried over sodium sulphate and brought to dryness. The residue is stirred several times with petroleum ether, the combined filtrates are completely freed from the solvent and the residue is then left to crystallize. The title compound is obtained in 90% yield. Colourless crystals; m.p.: 76° C.
$^1$H-NMR (CDCl$_3$): δ(ppm)=1.52–2.98 (m; 8 H, C—H$_{aliphat}$), 2.30 (s; 3 H, N—CH$_3$), 5.12 (m; 1 H, —O—CH), 6.41 (d, $^3$J=8.4 Hz; 1 H, R$^5$=H) 7.32–7.77 (m; 4 H, C—H$_{aromat}$), 8.40 (d, $^3$J=8.4 Hz; 1 H, R$^4$=H).

Example 19:
N'-Methylpiperidin-3-yl isoquinolin-1(2 H)-one-N-carboxylate hydrochloride Hydrogen chloride is introduced at 0° C. into a solution of 5.72 g (20 mmol) of N'-methylpiperidin-3-yl isoquinolin-1(2 H)-one-N-carboxylate in 200 ml of diisopropyl ether until it is saturated, the suspension obtained is stirred at room temperature for a further 2 h, and the precipitate is then filtered off with suction under nitrogen, washed with diisopropyl ether and with petroleum ether and dried over phosphorus pentoxide in vacuo. The very hygroscopic title compound is obtained in quantitative yield.
Colourless powder; deliquesces in air
$^1$H-NMR (d6-DMSO): δ(ppm)=1.51–3.93 (m; 8 H, C—H$_{aliphat}$), 2.83 (s; 3 H, N—CH$_3$), 5.05 (m; 1 H, —O—CH), 6.63 (d, $^3$J=8 Hz; 1 H, R$^5$=H) 7.48–7.88 (m; 4 H, C—H$_{aromat}$), 8.25 (d, $^3$J=8 Hz; 1 H, R$^4$=H).
IR (KBr; cm$^{-1}$): 3425, 3065, 2950, 2673, 2555, 2512, 1772, 1672, 1631, 1602, 1461, 1406, 1329, 1292, 1256, 1230, 1197, 1148, 1130, 1102, 1091, 1042, 1007, 980, 954, 884, 788, 769, 685.

Example 20:
2'-Hydroxyethyl 1(2 H)-phthalazinone-N-carboxylate 5.85 g (40 mmol) of 1(2 H)-phthalazinone and 3.96 g (45 mmol) of ethylene carbonate are dissolved together in 50 ml of dimethylformamide and heated at about 150° to 160° C., (bath temp.) for 10 h. After cooling, the mixture is treated with 300 ml of water and extracted three times by shaking with 100 ml of ethyl acetate in each case, the combined organic phases are washed three times with 50 ml of water each time and dried over sodium sulphate, and the solvent is completely removed. The title compound crystallizes to 16% from xylene.

Slightly yellow crystals: m.p.: 107° C.

$^1$H-NMR (CDCl$_3$): δ=3.45 (t, $^3$J=4.3 Hz; 1 H, —CH$_2$—OH), 4.09(dt, $^3$J$_d$=4.3 Hz; $^3$HJ$_f$=4.8 Hz; 2 H, —CH$_2$—CH$_2$—OH), 4.45 (t, $^3$J$_f$=4.8 Hz; 2 H, —O—CH$_2$—CH$_2$—), 7.60–7.92 (m; 3 H, C—H$_{aromat}$), 8.17 (s; 1 H, R$^5$=H), 8.33–8.45 (m; 1 H, C—H$_{aromat}$).

IR (Nujol; cm$^{-1}$): 3375, 1632, 1580, 1284, 1250, 1148, 1071, 1049, 972, 918, 864, 762, 738, 684.

Example 21:

2'-Hydroxyethyl 1,2,3-benzotriazin-4(3 H)-one-N-carboxylate 11.77 g (80 mmol) of 1,2,3-benzotriazin-4(3 H)-one and 7.93 g (90 mmol) of ethylene carbonate are dissolved together in 50 ml of dimethylformamide and the mixture is heated for 10 hours at about 150 to 160° C. (bath temp.); the solvent is then removed in vacuo and the residue is stirred several times with petroleum ether and finally with diisopropyl ether until crystallization is complete.

The title compound crystallizes to 53% from xylene.

Slightly orange-coloured crystals; m.p.: 110° C.

Example 22:

Recipe for the production of tablets: 1000 tablets are prepared from the compounds below in the manner described below. One tablet then contains 100 mg of phenyl 1(2 H)-phthalazinone-N-carboxylate as active compound.

| | | |
|---|---|---|
| 1. | Phenyl 1(2H)-phthalazinone-N-carboxylate | 100 g |
| 2. | Lactose | 263 g |
| 3. | Microcrystalline cellulose | 120 g |
| 4. | Maize starch | 60 g |
| 5. | Magnesium stearate | 7 g |

1) and 2) are mixed, 3) and 4) are intermixed, 5) is added finally and mixed and the mixture is pressed directly.

Example 23:

Recipe for production of a cream:

The following recipe yields a 5% phenyl 1(2 H)-phthalazinone-N-carboxylate cream (substance data in % by weight):

| | |
|---|---|
| Phenyl 1(2H)-phthalazinone-N-carboxylate | 5.00 |
| Emulsifier (mixture of sodium glyceryl monostearate, sodium stearyl sulphate and sodium cetyl sulphate) | 10.00 |
| Medium-chain triglycerides | 6.25 |
| Myristyl alcohol | 5.00 |
| POE-12-cetylstearyl alcohol | 3.00 |
| Preservative | q.s. |
| Water | ad 100.00 |

We claim:

1. Compounds of the formula (I)

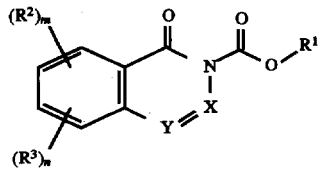

a)
 X denotes the group CR$^4$ and Y denotes the group CR$^5$, where
 R$^1$ represents a C$_1$- to C$_6$- lower alkyl group, a substituted C$_1$- to C$_6$- lower alkyl group, an aryl-C$_1$- to C$_6$- lower alkyl group, an aryl group or a heterocyclic group, R$^2$ and R$^3$ independently of one another represent the following groups:

hydrogen atoms, C$_1$- to C$_6$- lower alkyl groups, C$_1$- to C$_6$- lower alkoxy groups, C$_1$- to C$_6$- lower alkylthio groups, halogen atoms, nitro groups, hydroxyl groups, trifluoromethyl groups, cyano groups, sulpho groups, C$_1$- to C$_6$- lower alkoxycarbonyl groups, carboxylic acid groups, C$_1$- to C$_6$- lower alkoxycarbonyl groups, C$_1$- to C$_6$- lower alkoxycarbonyloxy groups, acetamido groups, benzamido groups or the group —N(R$^6$)R$^7$, R$^4$ and R$^5$ independently of one another represent a hydrogen atom, a C$_1$- to C$_6$- lower alkyl groups, a substituted C$_1$- to C$_6$- lower alkyl group, an aryl-C$_1$- to C$_6$- lower alkyl group or an aryl group, m and n independently of one another are equal to 0, 1, 2, 3, or 4, and R$^6$ and R$^7$ independently of one another represent a hydrogen atom or a C$_1$- to C$_6$- lower alkyl group, or in which b)
 X and Y denote e nitrogen atom, where
 R$^1$ represents a methyl group, a c$_3$- to c$_6$- lower alkyl group, a substituted C$_1$- to C$_6$- lower alkyl group, an aryl-C$_1$- to C$_6$- lower alkyl group, an aryl group or a heterocyclic group, R$^2$ and R$^3$ independently of one another represent the following groups:

hydrogen atoms, C$_1$- to C$_6$- lower alkyl groups, C$_1$- to C$_6$- lower alkoxy groups, C$_1$- to C$_6$- lower alkylthio groups, halogen atoms, nitro groups, hydroxyl groups, trifluoromethyl groups, cyano groups, sulpho groups, C$_1$- to C$_6$- lower alkylsulphonyl groups, carboxylic acid groups, C$_1$- to C$_6$- lower alkoxycarbonyl groups, C$_1$- to C$_6$- lower alkoxycarbonyloxy groups, acetamido groups, benzamido groups or the group —N(R$^6$)RT$^7$, and m and n, R$^6$ and R$^7$ have the meanings mentioned under a), with the proviso that is R$^1$ denotes a methyl group, an unsubstituted C$_3$- to C$_6$- lower alkyl group, a phenyl group or a benzyl group, at least one group R$^2$ or R$^3$ is different from a hydrogen atom or a halogen atom, or in which c)
 X denotes a nitrogen atom and Y denotes the group CR$^5$, where
 R$^1$ represents a substituted C$_1$- to C$_6$- lower alkyl group, an aryl-C$_1$- to C$_6$- lower alkyl group, an aryl group or a heterocyclic group, R$^2$ and R$^3$ independently of one another have the meanings mentioned under a), R$^5$ represents a hydrogen atom or a C$_1$- to C$_6$- lower alkyl group, and m and n, R$^6$ and R$^7$ have the meanings mentioned under a), or in which d)
 X denotes a nitrogen atom and Y denotes the group CR$^5$, where
 R$^1$ represents a C$_1$- to C$_6$- lower alkyl group, a substituted C$_1$- to C$_6$- lower alkyl group, an aryl-C$_1$- to C$_6$- lower alkyl group, an aryl group or a heterocyclic group, R$^2$ and R$^3$ independently of one another have the meanings mentioned under a), $R^5$ represents a substituted $C_1$- to $C_6$- lower alkyl group, an aryl-$C_1$- to $C_6$- lower alkyl group or an aryl group, and m and n, $R^6$ and $R^7$ have the meanings mentioned under a), or in which e)

Y denotes a nitrogen atom and X denotes the group $CR^4$, where $R^1$ represents a $C_1$- to $C_6$- lower alkyl group, a substituted $C_1$- to $C_6$- lower alkyl group, an aryl-$C_1$- to $C_6$- lower alkyl, group, an aryl group or a heterocyclic group, $R^2$ and $R^3$ independently of one another have the meanings mentioned under a), $R^4$ represents a substituted $C_1$- to $C_6$- lower alkyl group other than an ethyl ester or a group of the formula (II)

$$-Z-R^8 \qquad (II)$$

where Z represents a carbonyl or carboxyl group, a sulfur atom or an oxygen atom and $R^8$ represents a $C_1$- to $C_6$- lower alkyl group, a substituted $C_1$- to $C_6$- lower alkyl group, an aryl-$C_1$- to $C_6$- lower alkyl group or an aryl group, and m and n, $R^6$ and $R^7$ have the meanings mentioned under a), or in which f)

Y denotes a nitrogen atom and X denotes the group $CR^4$, where $R^1$ represents a $C_1$- to $C_6$- lower alkyl group, an aryl group or a heterocyclic group, $R^2$ and $R^3$ independently of one another have the meanings mentioned under a), $R^4$ represents a hydrogen atom, a $C_1$- to $C_6$- lower alkyl group, a substituted $C_1$- to $C_6$- lower alkyl group, an aryl-$C_1$- to $C_6$- lower alkyl group or an aryl group, and m and n, $R^6$ and $R^7$ have the meanings mentioned under a), with the proviso that if $R^2$, $R^3$ and $R^4$ denote hydrogen atoms, $R^1$ is different from an unsubstituted phenyl group, and their salts with physiologically acceptable acids and bases.

2. Compounds of the formula (I) according to claim 1, wherein X denotes the group $CR^6$ and Y denotes the group $CR^5$, and $R^1$, $R^2$, $R^3$, $R^4$, $R^5$, m and n have the meanings set forth in claim 1a.

3. Compounds of the formula (I) according to claim 1, wherein X and Y denote a nitrogen atom, and $R^1$, $R^2$, $R^3$, m and n have the meanings set forth in claim 1b.

4. Compounds of the formula (I) according to claim 1, wherein X denotes a nitrogen atom and Y denotes the group $CR^5$, and $R^1$, $R^2$, $R^3$, $R^5$, m and n have the meanings set forth in claim 1c.

5. Compounds of the formula (I) according to claim 1, wherein X denotes a nitrogen atom and Y denotes the group $CR^5$, and $R^1$, $R^2$, $R^3$, $R^5$, m and n have the meanings set forth in claim 1d.

6. Compounds of the formula (I) according to claim 1, wherein Y denotes a nitrogen atom and X denotes the group $CR^4$, and $R^1$, $R^2$, $R^3$, $R^4$, $R^8$, m and n have the meanings set forth in claim 1e.

7. Compounds according to claim 2, wherein $R^4$ and $R^5$ denote a hydrogen atom.

8. Compounds according to claim 3, wherein $R^2$ and $R^3$ denote hydrogen atoms.

9. Compounds of the formula (I)

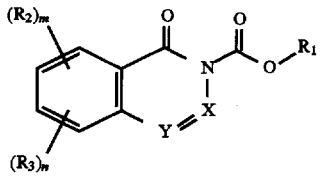

wherein X and Y denote a nitrogen atom, $R^1$ denotes a substituted $C_1$- to $C_6$- lower alkyl group, an aryl $C_1$- to $C_6$- lower alkyl group, an aryl group or a heterocyclic group, $R^2$ and $R^3$ independently of one another represent the following groups:

hydrogen atoms, $C_1$- to $C_6$- lower alkyl groups, $C_1$- to $C_6$- lower alkoxy groups, $C_1$- to $C_6$- lower alkylthio groups, halogen atoms, nitro groups, hydroxyl groups, trifluoromethyl groups, cyano groups, sulpho groups, $C_1$- to $C_6$- lower alkylsulphonyl groups, carboxylic acid groups, $C_1$- to $C_6$- lower alkoxycarbonyl groups, acetamido groups, benzamido groups or the group $-N(R^6)R^7$, $R^4$ and $R^5$ independently of one another represent a hydrogen atom, a $C_1$- to $C_6$- lower alkyl group, a substituted $C_1$- to $C_6$- lower alkyl group, an aryl-$C_1$- to $C_6$- lower alkyl group, or an aryl group, m and n independently of one another are equal to 0, 1, 2, 3, or 4, and $R^6$ and $R^7$ independently of one another represent a hydrogen atom or a $C_1$- to $C_6$- lower alkyl group.

10. Compounds according to claim 4, wherein $R^1$ denotes a substituted $C_1$- to $C_6$- lower alkyl group.

11. Compounds according to claim 4, wherein $R^1$ denotes an aryl group.

12. Compounds according to claim 6, wherein $R^4$ had the meaning of formula (II) and ZX represents a sulfur atom or carboxyl group.

13. Compounds according to claim 6, wherein $R^1$ denotes an aryl group or a heterocyclic group.

14. Process for the preparation of compounds of formula (I), comprising reacting a compound of the formula (III)

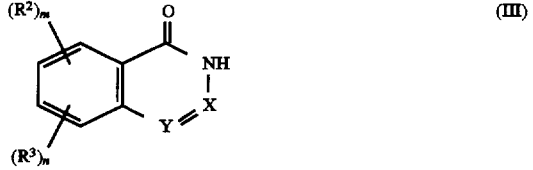

in which X, Y, $R^2$, $R^3$, , and n have the meanings as in claim 1, in the presence of a base with the appropriate haloformic acid esters of the formula

in which $R^1$ has the meaning as in claim 1, and Hal has the meaning fluorine or chlorine atoms.

15. A pharmaceutical composition comprising one or more compounds set forth in claim 1 and a pharmaceutically acceptable carrier therefor.

* * * * *